(12) United States Patent
Tanida

(10) Patent No.: US 11,501,849 B2
(45) Date of Patent: Nov. 15, 2022

(54) METHOD FOR CALCULATING BINDING FREE ENERGY, CALCULATION DEVICE, AND PROGRAM

(71) Applicant: FUJITSU LIMITED, Kawasaki (JP)

(72) Inventor: Yoshiaki Tanida, Kawasaki (JP)

(73) Assignee: FUJITSU LIMITED, Kawasaki (JP)

(\*) Notice: Subject to any disclaimer, the term of this patent is extended or adjusted under 35 U.S.C. 154(b) by 432 days.

(21) Appl. No.: 15/860,134

(22) Filed: Jan. 2, 2018

(65) Prior Publication Data

US 2018/0121598 A1    May 3, 2018

Related U.S. Application Data

(63) Continuation of application No. PCT/JP2015/071031, filed on Jul. 23, 2015.

(51) Int. Cl.
*G16B 15/00* (2019.01)
*G16B 5/00* (2019.01)
*G16B 15/20* (2019.01)
*G16B 5/30* (2019.01)

(52) U.S. Cl.
CPC .......... *G16B 15/00* (2019.02); *G16B 5/00* (2019.02); *G16B 15/20* (2019.02); *G16B 5/30* (2019.02)

(58) Field of Classification Search
CPC .......... G16B 15/00; G16B 5/00; G16B 15/20; G16B 5/30
USPC .................................................. 703/2
See application file for complete search history.

(56) References Cited

U.S. PATENT DOCUMENTS

| 6,178,384 B1* | 1/2001 | Kolossváry ............ G16C 20/30 703/11 |
| 2007/0166760 A1 | 7/2007 | Umeyama et al. |
| 2008/0032419 A1 | 2/2008 | Eguchi et al. |
| 2014/0288899 A1 | 9/2014 | Tanida |

FOREIGN PATENT DOCUMENTS

| JP | 2005-242493 | 9/2005 |
| JP | 2006-28038 | 2/2006 |
| JP | 2012-83966 | 4/2012 |
| JP | 2014-186468 | 10/2014 |

OTHER PUBLICATIONS

David L. Mobley, John D. Chodera, and Ken A. Dil, On the use of orientational restraints and symmetry corrections in alchemical free energy calculations (2006), J Chem Phys. Aug. 28, 2006; 125(8): 084902.*

(Continued)

*Primary Examiner* — John E Johansen
(74) *Attorney, Agent, or Firm* — Staas & Halsey LLP

(57) ABSTRACT

A method for calculating binding free energy, where the method includes a plurality of steps each including adding a distance restraint potential between a binding calculation target molecule and a target molecule, wherein the method is a method for calculating binding free energy between the binding calculation target molecule and the target molecule using a computer, and wherein anchor points of the binding calculation target molecule in the plurality of the steps are identical anchor points, and anchor points of the target molecule in the plurality of the steps are different anchor points.

13 Claims, 8 Drawing Sheets

(56) References Cited

OTHER PUBLICATIONS

Pär Söderhjelm, Gareth A. Tribello, Michele Parrinello, Ligand binding with reconnaissance metadynamics Proceedings of the National Academy of Sciences Apr. 2012, 109 (14) 5170-5175; DOI: 10.1073/pnas.1201940109.*
Vendruscolo M, Dobson CM. Towards complete descriptions of the free-energy landscapes of proteins. Philos Trans A Math Phys Eng Sci. Feb. 15, 2005;363(1827):433-50; discussion 450-2. doi: 10.1098/rsta.2004.1501. PMID: 15664892.*
Wang, Jiyao & Deng, Yuqing & Roux, Benoît. (2006). Absolute Binding Free Energy Calculations Using Molecular Dynamics Simulations with Restraining Potentials. Biophysical journal. 91. 2798-814. 10.1529/biophysj.106.084301.*
David L. Mobley, John D. Chodera, and Ken A. Dil, On the use of orientational restraints and symmetry corrections in alchemical free energy calculations (2006), J Chem Phys. Aug. 28, 2006; 125(8): 084902roceedings of the National Academy of Sciences Apr. 2013, 110 (16) 6358-6363.*
Accurate binding free energies from funnel metaDynamics, Vittorio Limongelli, Massimiliano Bonomi, Michele Parrinello Proceedings of the National Academy of Sciences Apr. 2013, 110 (16) 6358-6363.*
Pontiggia, F., Pachov, D., Clarkson, M. et al. Free energy landscape of activation in a signalling protein at atomic resolution. Nat Commun 6, 7284 (2015).*
Wang, Jiyao & Deng, Yuqing & Roux, Benoît. (2006). Absolute Binding Free Energy Calculations Using Molecular Dynamics Simulations with Restraining Potentials. Biophysical journal. 91. 2798-814. 10.1529/biophysj.106.084301. (Year: 2006).*
David L. Mobley, John D. Chodera, and Ken A. Dil, On the use of orientational restraints and symmetry corrections in alchemical free energy calculations (Year: 2006).*
Accurate binding free energies from funnel metaDynamics, Vittorio Limongelli, Massimiliano Bonomi, Michele Parrinello Proceedings of the National Academy of Sciences Apr. 2013, 110 (16) 6358-6363 (Year: 2013).*
Pontiggia, F., Pachov, D., Clarkson, M. et al. Free energy landscape of activation in a signalling protein at atomic resolution. Nat Commun 6, 7284 (Year: 2015).*
Telesio (Non-Patented Literature, Molecular Simulation of Transport Proteins in Interaction with Physiological and Pharmacological Ligands) (Year: 2014).*
Kaus, et al., "How to Deal with Multiple Binding Poses in Alchemical Relative Protein-Ligand Binding Free Energy Calculations," Journal of Chemical Theory and Computation 2015, XP055487582, pp. 2670-2679.
Mobley, et al., "On the use of orientational restraints and symmetry corrections in alchemical free energy calculations," National Institute of Health Public Access, Journal of Chemical Physics, vol. 125, No. 8, Aug. 28, 2006, XP055487548, 30pgs.
Extended European Search Report dated Jul. 10, 2018, in corresponding European Patent Application No. 15898960.8, 10 pgs.
Yoshiaki Tanida, "Binding Free Energy Calculations for Theophylline/Caffeine to RNA Aptamer," J. Comput. Chem. Jpn., vol. 13, No. 3, Sep. 30, 2014, pp. 193-195.
Amy C. Anderson, "The Process of Structure-Based Drug Design," Chemistry & Biology, vol. 10, Sep. 2003, pp. 787-797.
International Search Report dated Oct. 27, 2015 in corresponding International Patent Application No. PCT/JP2015/071031.
Written Opinion of the International Searching Authority dated Oct. 27, 2015 in corresponding International Patent Application No. PCT/JP2015/071031.
Kaus, et al., "How to Deal with Multiple Binding Poses in Alchemical Relative Protein-Ligand Binding Free Energy Calculations," Journal of Chemical Theory and Computation 2015, XP055439585, pp. 2670-2679.

* cited by examiner

METHOD FOR CALCULATING BINDING FREE ENERGY, CALCULATION DEVICE, AND PROGRAM

CROSS-REFERENCE TO RELATED APPLICATION

This application is a continuation application of International Application PCT/JP2015/071031 filed on Jul. 23, 2015 and designated the U.S., the entire contents of which are incorporated herein by reference.

FIELD

The embodiments discussed herein relate to a method and device for calculating binding free energy between a target molecule and a binding calculation target molecule, and a program for executing the method.

BACKGROUND

In recent years, simulations have been performed by various computers in order to reduce enormous costs and efforts spent on experimentally searching drug candidate molecules. The search of a drug candidate molecule is to search a compound (ligand) that strongly interacts with a target molecule associated with a target disease (a targeted disease) as a drug candidate. Screening of a compound based on a target molecular steric structure by means of a computer has been actively performed.

Particularly frequently used methods include structure-based drug design (SBDD) (see, for example, The Process of Structure-Based Drug Design", A. C. Anderson, Chemistry & Biology, 10, 787 (2003)). The above-mentioned method is a molecule design method based on conformation information of a target molecule or a receptor.

When a drug candidate molecule to be bound to a target molecule is designed using a computer, it is important to quantitatively predict binding activity (binding free energy) of a drug candidate molecule or a fragment of a drug candidate molecule (in the present specification, the drug candidate molecule and the fragment are collectively referred to as a binding calculation target molecule) against a target molecule, in order to efficiently perform feedback to molecular design. In the quantitative prediction of the binding activity, calculation needs to be performed with maintaining a relationship to a standard state in order to directly compare with an experimental value.

Accordingly, in the art, a potential for restraining a distance between a target molecule and a calculation target molecule has been introduced to limit a structural space the molecules can take.

However, in the art, there is often a case where calculation accuracy of binding free energy between the target molecule and the binding calculation target is lowered.

SUMMARY

The disclosed calculation method of binding free energy includes a plurality of steps each including adding a distance restraint potential between a binding calculation target molecule and a target molecule, wherein the method is a method for calculating binding free energy between the binding calculation target molecule and the target molecule using a computer, and wherein anchor points of the binding calculation target molecule in the plurality of the steps are identical anchor points, and anchor points of the target molecule in the plurality of the steps are different anchor points.

The disclosed program is a program for causing a computer to execute calculation of binding free energy between a binding calculation target molecule and a target molecule. The program includes executing a plurality of steps each including adding a distance restraint potential between the binding calculation target molecule and the target molecule, wherein anchor points of the binding calculation target molecule in the plurality of the steps are identical anchor points, and anchor points of the target molecule in the plurality of the steps are different anchor points.

The disclosed device for calculating binding free energy is a device for calculating binding free energy between a binding calculation target molecule and a target molecule. The device includes an adding unit configured to perform a plurality of steps each including adding a distance restraint potential between the binding calculation target molecule and the target molecule, wherein anchor points of the binding calculation target molecule in the plurality of the steps are identical anchor points, and anchor points of the target molecule in the plurality of the steps are different anchor points.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS (Method for Calculating Binding Free Energy)

The disclosed method for calculating binding free energy is a method for calculating binding free energy between a binding calculation target molecule and a target molecule using a computer.

The inventors of the disclosed technology have studied about a cause for reduction in calculation accuracy when binding free energy between a binding calculation target molecule and a target molecule is calculated by utilizing addition of a distance restraint potential.

First, binding free energy between a target molecule and a binding calculation target molecule was calculated according to the alchemical route calculation method utilizing addition of a distance restraint potential.

As the target molecule, RNA was used. As the binding calculation target molecule, a theophylline molecule was used. As a complex structure of the RNA and the theophylline molecule, 1O15 stored in the protein data bank (PDB) was used.

As a force field of the RNA, AMBER99/parmbsc0 was used. Moreover, a structure of the theophylline molecule was optimized in vacuum using 6-31G* basis, and RESP was used for point charge and general amber force field (GAFF) was used for a force field.

A center of gravity of the theophylline molecule was treated as an anchor point of the theophylline molecule.

An anchor point of the RNA was determined as the coordinates of the atom of U23 C1'.

Calculation was performed according to the molecular dynamic method using Gromacs.

Figure 1:
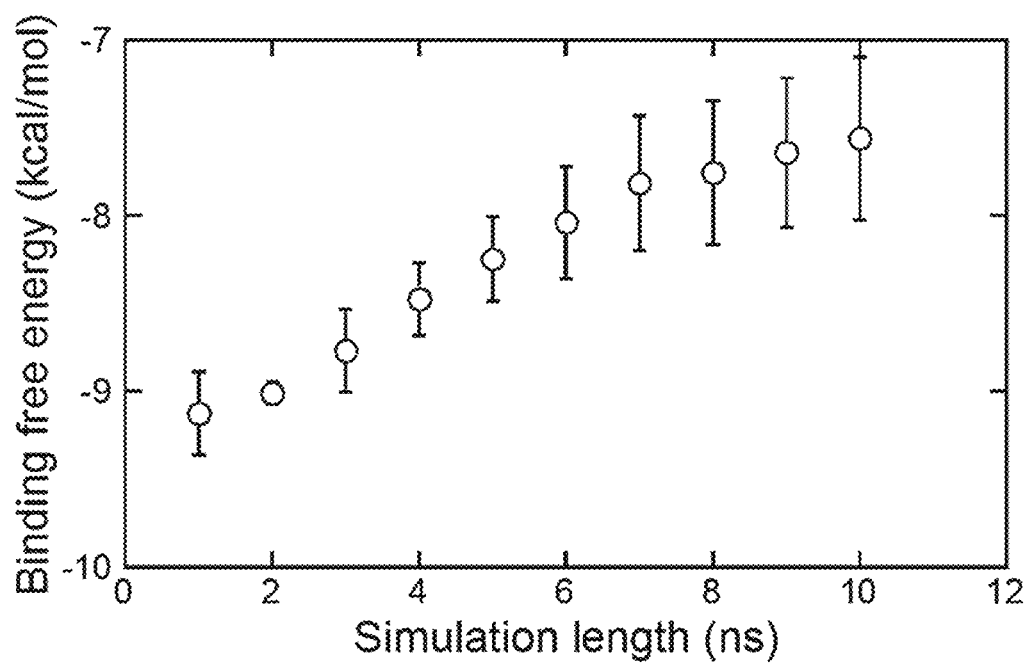
FIG. 1 illustrates one example of results of known calculation of binding free energy.

The results are presented in FIG. 1. In FIG. 1, the horizontal axis represents simulation time (ns), and each plot represents a binding free energy value from 0.5 ns to the plotted time. Specifically, the plot of 1 ns represents a binding free energy value for the time from 0.5 ns to 1 ns, and the plot of 10 ns represents a binding free energy value for the time from 0.5 ns to 10 ns. It can be conformed from FIG. 1 that the binding free energy value is not stabilized even when the calculation time is elapsed.

Moreover, the binding free energy of the above-mentioned system is −8.9 kcal/mol according to the experimental result. On the other hand, the binding free energy of the result of FIG. 1 is −7.56±0.47 kcal/mol (the plot of 10 ns).

Accordingly, the above calculation has low calculation accuracy.

The present inventors have speculated the cause as follows.

The present inventors have speculated that calculation accuracy of binding free energy lowers when a plurality of stable structures (binding pauses) are present in a binding structure between a target molecule and a binding calculation target molecule, in the case where addition of a distance restraint potential is utilized in calculation of the binding free energy.

Figure 2A:
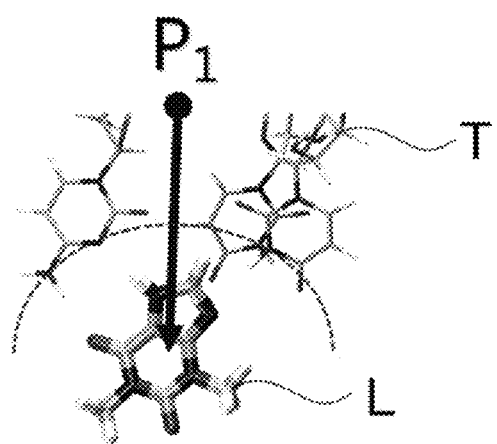
FIG. 2A illustrates one example of a stable structure when a distance restraint potential is set.
Figure 2B:
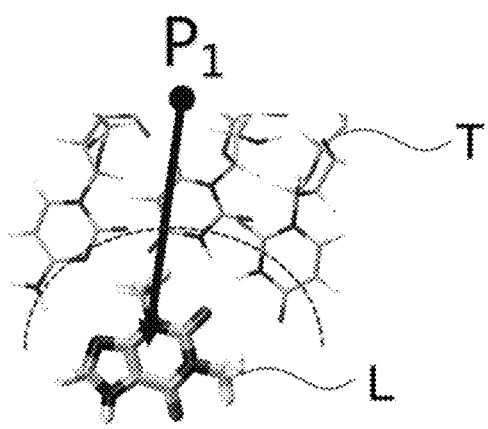
FIG. 2B illustrates another example of a stable structure when a distance restraint potential is set.

Specifically, when one distance restraint potential is set as illustrated in FIG. 2A and FIG. 2B and there are 2 or more stable structures the target molecule T and the binding calculation target molecule L can take, calculation accuracy of binding free energy lowers. The present inventors have speculated as mentioned above. In FIG. 2A and FIG. 2B, $P_1$ is an anchor point of the target molecule T.

The present inventors performed researches to support the speculation above.

Figure 3:
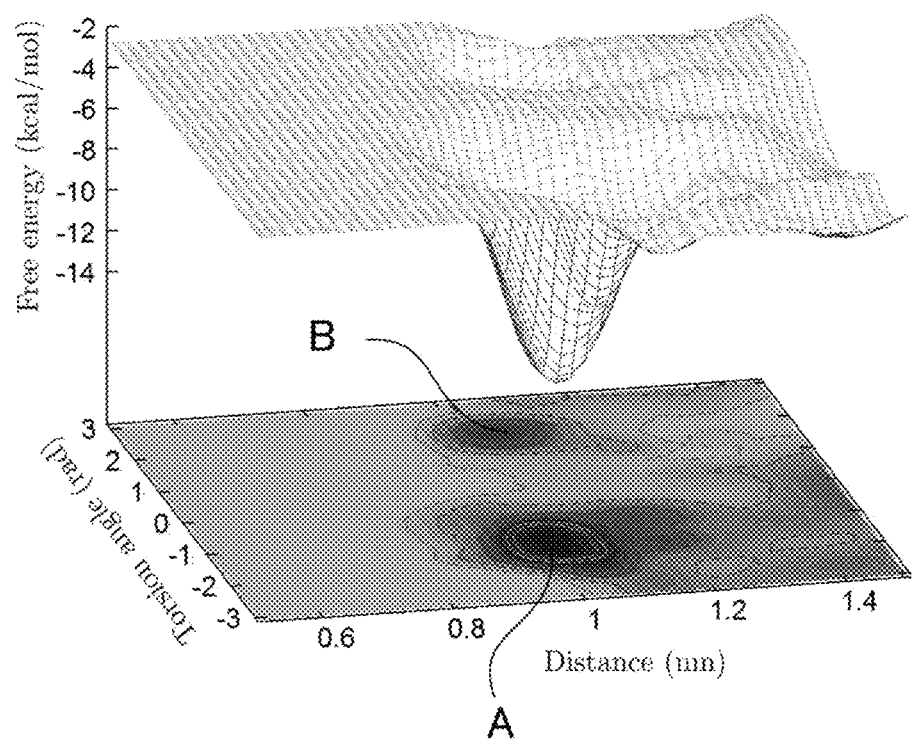
FIG. 3 illustrates one example of a binding free energy landscape.

A structural space of a complex of a theophylline molecule and RNA was searched using metadynamics. The result is presented in FIG. 3. FIG. 3 depicts a binding free energy landscape.

It can be understood from the binding free energy landscape that there are two stable structures (A and B), where the stable structure B is in a metastable state) having similar sizes. It is desirable that a calculation value according to an abundance ratio between the two stable structures (A and B) is calculated. In actual calculation, however, a calculation value according to the abundance ratio of the two stable structures cannot be calculated because there is a case where the binding free energy is localized to one of the stable structures. Accordingly, calculation accuracy lowers.

The insight above and the outline of the disclosed technology based on the insight are described with reference to schematic diagrams.

Figure 4A:
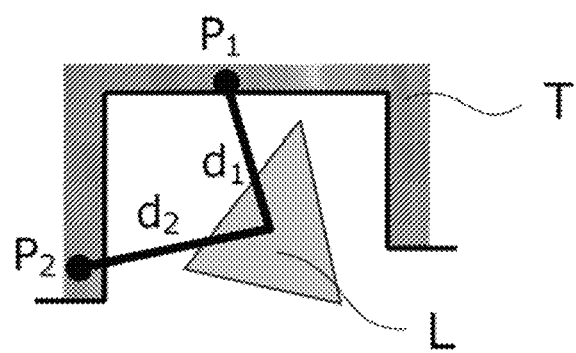
FIG. 4A is a schematic diagram illustrating a binding structure between a target molecule T and a binding calculation target molecule L.

FIG. 4A is a schematic diagram of a binding structure between a target molecule T and a binding calculation target molecule L. In FIG. 4A, the binding calculation target molecule L is present within a binding site of the target molecule T.

Figure 4B:
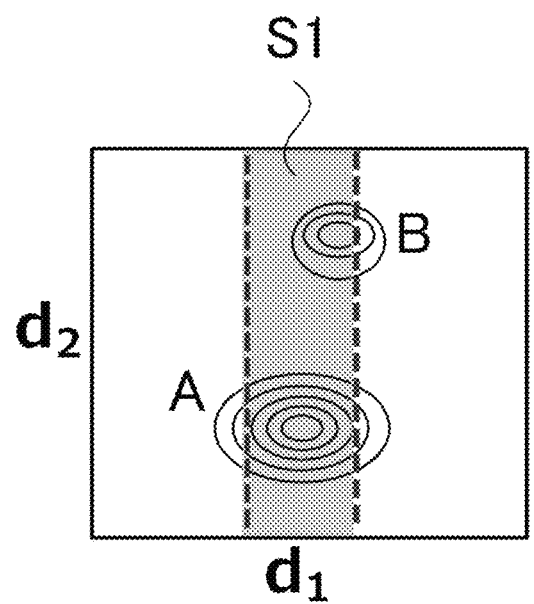
FIG. 4B is a schematic diagram illustrating a binding free energy surface.
Figure 4C:
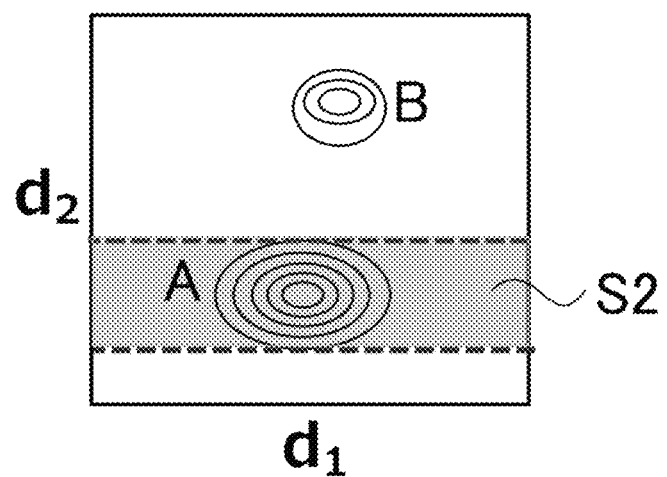
FIG. 4C is a schematic diagram illustrating a binding free energy surface.

When an anchor point of the target molecule T is determined as $P_1$, a distance restraint potential between the target molecule T and the binding calculation target molecule L is determined as P1. When an anchor point of the target molecule is determined as $P_2$ ($P_2$ is different from $P_1$), a distance restraint potential between the target molecule T and the binding calculation target molecule L is determined as P2. Then, distances restrained by the distance restraint potentials P1 and P2 are respectively determined as $d_1$ and $d_2$. In the manner as described, schematic diagrams of the binding free energy surface are produced (FIG. 4B and FIG. 4C). Note that, the distances $d_1$ and $d_2$ are generally not fixed values, and are each within a certain numerical range.

As illustrated in FIG. 4B, the sampling space S1 in case of the distance restraint potential P1 includes a stable structure B in a metastable state, in addition to a stable structure A. In calculation of binding free energy using the distance restraint potential P1, therefore, calculation accuracy lowers due to an influence of the stable structure B (FIG. 1).

As illustrated in FIG. 4C, on the other hand, the sampling space S2 in case of the distance restraint potential P2 includes a stable structure A, but not a stable structure B in a metastable state. In calculation of binding free energy using the distance restraint potential P2, therefore, excellent calculation accuracy is achieved without being influenced by the stable structure B.

Figure 5:
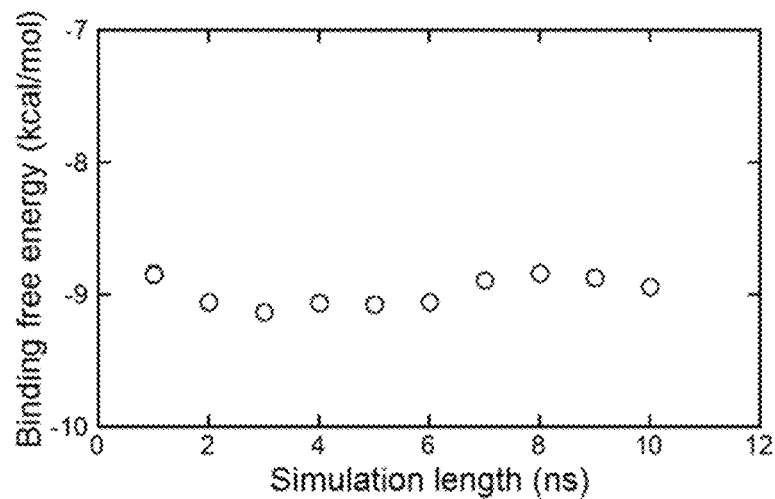
FIG. 5 depicts results of calculation of binding free energy in case of a distance restraint potential P2.

The calculation results of binding free energy in case of the distance restraint potential P2 are depicted in FIG. 5. The calculation was performed in the same manner as the above-described calculation of binding free energy between the theophylline and the RNA, except that the anchor point of the RNA was changed to the coordinates of the atom of A7C4'.

The results are presented in FIG. 5. In FIG. 5, the horizontal axis represents simulation time (ns), and each plot represents a binding free energy value from 0.5 ns to the plotted time. Specifically, the plot of 1 ns represents a binding free energy value for the time from 0.5 ns to 1 ns, and the plot of 10 ns represents a binding free energy value for the time from 0.5 ns to 10 ns. It can be conformed from FIG. 5 that the binding free energy value is stabilized regardless of the calculation time.

The binding free energy of the above-mentioned system is −8.9 kcal/mol according to the experimental result. On the other hand, the binding free energy of the result of FIG. 5 is −8.94±0.04 kcal/mol (the plot of 10 ns).

Specifically, the calculation of binding free energy using the distance restraint potential P2 can calculate more stable binding free energy (excellent calculation accuracy), compared to the calculation of binding free energy using the distance restraint potential P1.

Accordingly, calculation accuracy of binding free energy can be improved when the method includes a plurality of steps each including adding a distance restraint potential between a binding calculation target molecule and a target molecule, and anchor points of the binding calculation target molecule in the plurality of the steps are identical anchor points, and anchor points of the target molecule in the plurality of the steps are different anchor points.

The calculation of the binding free energy is not particularly limited as long as the calculation is a method using a distance restraint potential, and may be appropriately selected depending on the intended purpose. The calculation is more preferably performed according to the alchemical route calculation method. The alchemical route calculation method is also called as alchemical free energy calculation or alchemical transformation, and is a method for calculating binding free energy using a thermodynamic cycle along a virtual (alchemical) path.

For example, the alchemical route calculation method is introduced in Adv Protein Chem Struct Biol. 2011; 85: 27-80.

Figure 6:
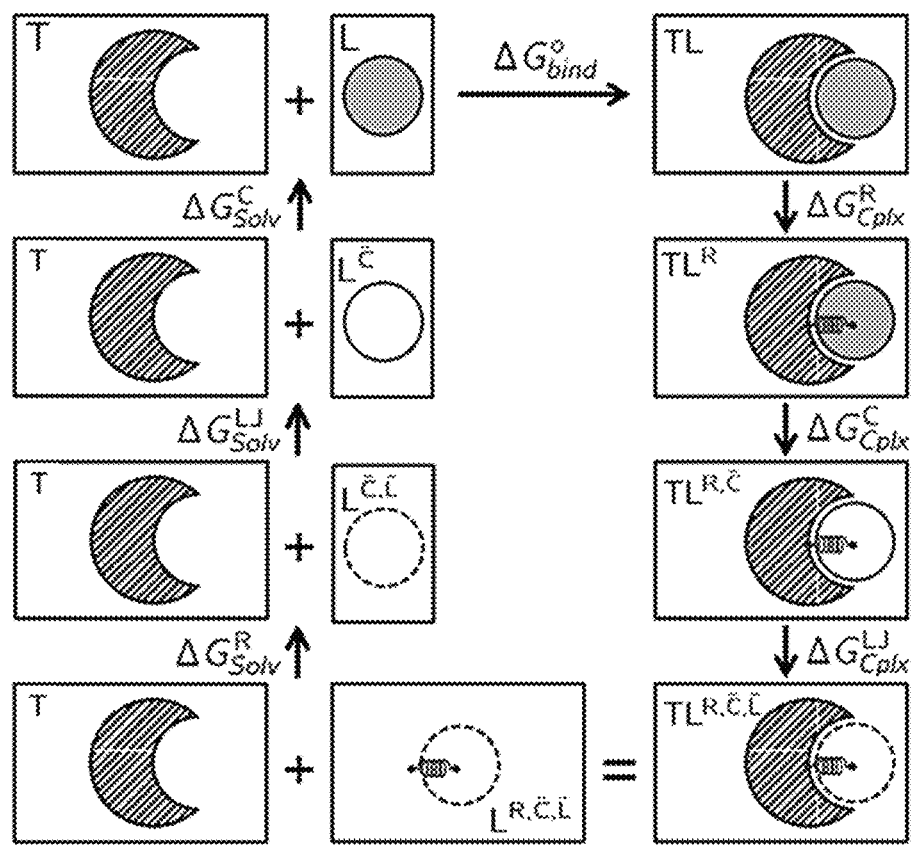
FIG. 6 is a conceptual diagram illustrating one example of the alchemical route calculation method.

Examples of the alchemical route calculation method include a calculation method determined by FIG. 6 and the following equation.

$$\Delta G_{bind}{}^O = -(\Delta G_{Solv}{}^C + \Delta G_{Solv}{}^{LJ} + \Delta G_{Sol}{}^R + \Delta G_{Cplx}{}^R + \Delta G_{Cplx}{}^C + \Delta G_{Cplx}{}^{LJ})$$

In FIG. 6, the crescent-shaped object is a target molecule (T) and the circular object is a binding calculation target molecule (L). In the equation above and FIG. 1, C represents electrostatic interaction, LJ represents Van der Waals interaction, Solv represents a solvent, Cplx represents a complex of the target molecule (T) and the binding calculation target molecule (L), and R represent a spring restraint potential.

In the right side of the equation above, the first, second, fourth, fifth, and sixth items can be evaluated, for example, by the Bennett Acceptance Ratio (BAR) method.

Note that, binding free energy of a binding calculating target molecule and a target molecule is typically binding free energy between the binding calculation target molecule and the target molecule that are in a solvent. The solvent is typically water.

Calculation of binding free energy is performed using a computer. The number of the computers used for calculation of the binding free energy may be one, or two or more. For example, calculation of the binding free energy may be performed dividedly by a plurality of computers.

<Distance Restraint Potential Adding Step>

The method for calculating binding free energy includes a plurality of steps each including adding a distance restraint potential between the binding calculation target molecule and the target molecule.

Anchor points of the binding calculation target molecule in the plurality of the steps are identical anchor points.

Anchor points of the target molecule in the plurality of the steps are different anchor points. Specifically, in each of a plurality of steps each adding a distance restraint potential, a different anchor point is used as the anchor point of the target molecule.

<<Binding Calculation Target Molecule>>

The binding calculation target molecule means a drug candidate molecule, or a fragment for designing a drug candidate molecule.

For example, the fragment is used for fragment-based drug design (FBDD).

<<Target Molecule>>

The target molecule is not particularly limited and may be appropriately selected depending on the intended purpose. Examples of the target molecule include protein, ribonucleic acid (RNA), and deoxyribonucleic acid (DNA).

<<Distance Restraint Potential>>

The distance restraint potential is not particularly limited as long as the distance restraint potential is a potential for restraining a distance between the binding calculation target molecule and the target molecule, and may be appropriately selected depending on the intended purpose. Examples of the distance restraint potential include restraint potentials by springs. The binding force is not particularly limited and may be appropriately selected depending on the intended purpose.

The distance restraint potential is added between the binding calculation target molecule and the target molecule using an anchor point of the binding calculation target molecule and anchor points of the target molecule.

A plurality of distance restraint potentials added between one anchor point of the binding calculation target molecule and a plurality of anchor points of the target molecule may be each independently set according to a distance between the two anchor points. For example, a distance restraint potential is determined in a manner that a size of fluctuations of the binding calculation target molecule is within a certain range.

The distance restriction between the binding calculation target molecule and the target molecule is performed in order to accurately consider a degree of freedom of translational motions of a molecule contributing the most to binding activity.

Accordingly, it is logical that a center of gravity of the binding calculation target molecule is set as an anchor point of the binding calculation target molecule. For example, a center of gravity of the binding calculation target molecule can be determined by the following equation.

$$\vec{x}_{com} = \frac{\sum m_i \vec{x}_i}{\sum m_i}$$

In the equation, m represents a mass, and x represents coordinates of an atom constituting the binding calculation target molecule.

Since a hydrogen atom is light, the hydrogen atom hardly affect a position of a center of gravity determined. Accordingly, a center of gravity of the binding calculation target molecule is preferably determined by excluding hydrogen atoms constituting the binding calculation target molecule because the calculation time can be shortened.

An anchor point of the target molecule is preferably determined using an atom having small fluctuations among atoms in the target molecule.

The atom is preferably an atom present within a range of 5 Å to 15 Å from an anchor point of the binding calculation target molecule, because the frequency distribution of the distance between the anchor points becomes close to a normal distribution, and further excellent calculation accuracy can be obtained.

The atom is an atom having small fluctuations.

For example, the atom having small fluctuations is selected by determining the root mean square fluctuation (RMSF) of atoms in the target molecule, and selecting the atom having small RMSF comparing each of the determined RMSF of the atoms.

For example, the root mean square fluctuation (RMSF) was determined on all of the atoms in the target molecule, excluding hydrogen atoms, and the atom having RMSF smaller than the arithmetic mean value of RMSF of all the atoms on which RMSF have been determined is selected as an atom having small fluctuations.

The RMSF of the atom having small fluctuations is preferably 1.0 Å or less.

Examples of the atom having small fluctuations include atoms in a main chain of the target molecule. The main chain means the longest chain in the target molecule. The atoms in the main chain have small fluctuations compared to atoms in side chains.

An anchor point of the target molecule may be a center of gravity of a plurality of atoms having small fluctuations in the target molecule. Note that, the plurality of atoms are preferably atoms within a range of 5 Å to 15 Å from an anchor point of the binding calculation target molecule. When atoms of a main chain of the target molecule are not present within a range of 5 Å to 15 Å from an anchor point of the binding calculation target molecule, for example, a plurality of atoms in a side chain that may have larger fluctuations than atoms in the main chain but have relatively small fluctuations among atoms in the target molecule may be used, and a center of gravity of such atoms of the side chain may be determined as an anchor point of the target molecule.

Examples of the number of atoms in the plurality of atoms include 2.

Examples of a calculation method of a center of gravity of the plurality of atoms include similar methods for a calculation method of a center of gravity of the binding calculation target molecule.

For example, the anchor point can be determined by means of a general computer system (e.g., various network servers, work stations, and personal computers) equipped with a central processing unit (CPU), random access memory (RAM), a hard disk, various peripherals, etc.

In the method for calculating binding free energy, a plurality of values of binding free energy between the binding calculation target molecule and the target molecule is preferably calculated using each of a plurality of distance restraint potentials added in the plurality of the steps.

In the method for calculating binding free energy, the smallest value of binding free energy among the calculated values of binding free energy is extracted and treated as a calculated result. For example, an operation of extraction can be performed by a computer.

In the method for calculating binding free energy, a plurality of anchor points of the target molecule are set. A method for setting anchor points is not particularly limited and may be appropriately selected depending on the intended purpose. For example, anchor points can be set in the following manner.

Figure 7:
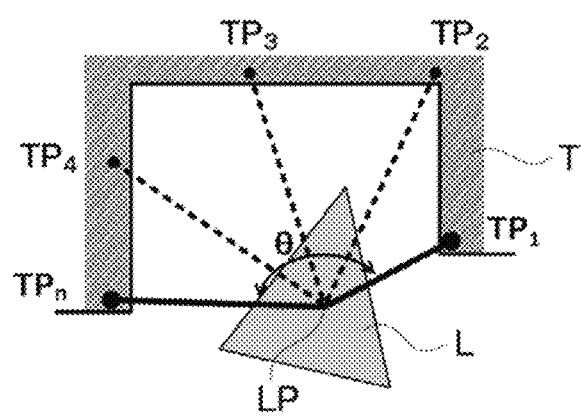
FIG. 7 is a schematic diagram for describing one example of a method for setting a plurality of anchor points of a target molecule.

As illustrated in FIG. 7, an anchor point LP of a binding calculation target molecule L is set. Subsequently, one anchor point $TP_1$ is set at an edge of a binding site of a target molecule T. Subsequently, another anchor point $TP_n$ is set the other edge of the binding site T. Then, an angle θ formed between the line segment between the anchor point LP and the anchor point $TP_1$ and the line segment between the anchor point LP and the anchor point $TP_n$ with the anchor point LP as an apex is equally divided into (n−1). Then, an anchor point of the target molecule is added per an angle θ/(n−1) which is given by equally dividing into (n−1). FIG. 7 illustrates a case where n=5, and three anchor points ($TP_2$, $TP_3$, and $TP_4$) are added.

Then, binding free energy between the target molecule T and the binding calculation target molecule L is calculated using each of a plurality of distance restraint potentials added between each of the 5 anchor points of the target molecule T and the anchor point LP.

Figure 8:
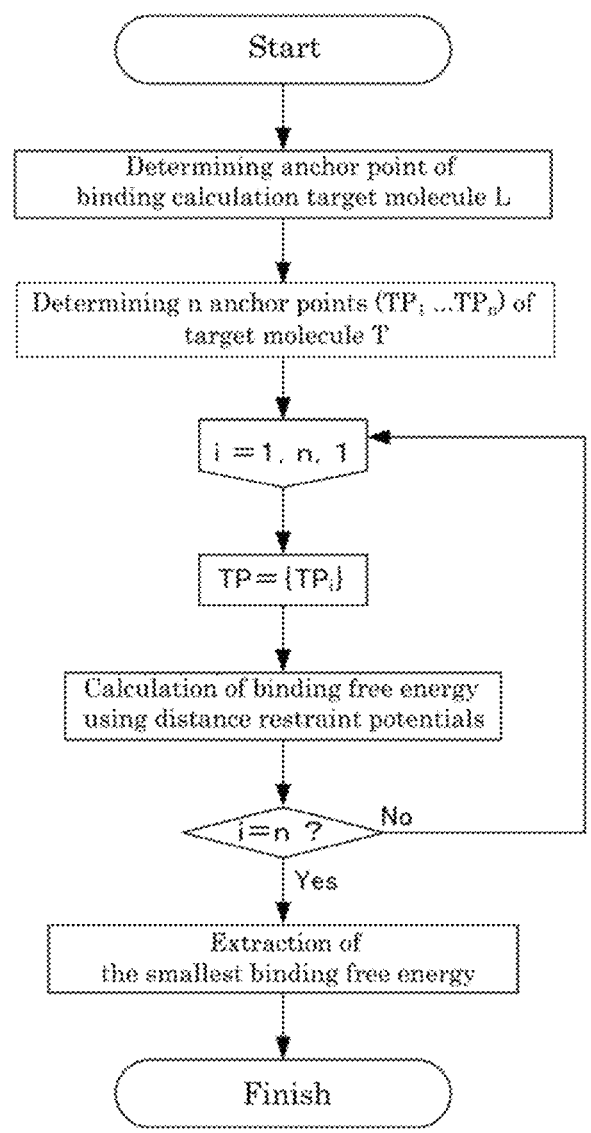
FIG. 8 is a flowchart describing one example of the disclosed method for calculating binding free energy.

One example of the method for calculating binding free energy is described with reference to a flowchart (FIG. 8).

First, an anchor point of a binding calculation target molecule L is determined. For example, the anchor point is set as a center of gravity of the binding calculation target molecule L.

Next, anchor points of a target molecule T are determined. The number of the anchor points is plural (n). The number of the anchor points may be appropriately selected depending on a target molecule that is a subject of calculation, a binding calculation target molecule that is a subject of calculation, calculation time, and a purpose of calculation. A method for determining the plurality of anchor points is not particularly limited and may be appropriately selected depending on the intended purpose. Examples of the method include the method described using FIG. 7.

Next, calculation of binding free energy is performed using each of distance restraint potentials added between each of n pieces of anchor points of the target molecule T and the anchor point of the binding calculation target molecule L. Accordingly, calculation of binding free energy is performed n times. At the time of calculation, for example, the numbers are given to the n pieces of the anchor points as 1, 2, . . . (n−1), and n, and calculation of binding free energy is performed in the order of the number.

Next, the calculation results of the calculation of binding free energy performed n times are compared, and the smallest value of the binding free energy is extracted.

In the manner as described, one example of the calculation of binding free energy is completed.

For example, the method for calculating binding free energy can be performed using the molecular orbital method or the molecular dynamics method.

Examples of molecular orbital calculation according to the molecular orbital method include nonempirical molecular orbital calculation (ab initio molecular orbital calculation), and semiempirical molecular orbital calculation.

Examples of a methodology of the nonempirical molecular orbital calculation include the Hartree-Fock method, and the electron correlation method.

Examples of a methodology of the semiempirical molecular orbital calculation include CNDO, INDO, AM1, and PM3.

Examples of a program of the nonempirical molecular orbital calculation include Gaussian03, GAMESS, ABINIT-MP, and Protein DF.

Examples of a program of the semiempirical molecular orbital calculation include MOPAC.

Examples of a program used for the molecular dynamics method include gromacs (gromacs: Groningen Machine for Chemical Simulations), associated model building with energy refinement (amber), charm, tinker, and lammps.

The method for calculating binding free energy can be performed by using a device for calculating binding free energy described later.

(Program)

The disclosed program is a program for allowing calculation of binding free energy between a binding calculation target molecule and a target molecule to be performed.

With the program, a plurality of steps each including adding a distance restraint potential between the binding calculation target molecule and the target molecule are executed.

With the program, anchor points in the binding calculation target molecules in the plurality of the steps are identical anchor points, and anchor points of the target molecules in the plurality of the steps are different anchor points.

The program is configured to execute the method for calculating binding free energy.

The program can be created using any of various programming languages known in the art according to a configuration of a computer system for use, a type or version of an operation system for use.

The program may be recorded on a storage medium, such as an integral hard disk, and an external hard disk, or recorded on a storage medium, such as a compact disc read only memory (CD-ROM), a digital versatile disk read only memory (DVD-ROM), a magneto-optical (MO) disk, and a universal serial bus (USB) memory stick (USB flash drive). In the case where the program is recorded on a storage medium, such as a CD-ROM, a DVD-ROM, an MO disk, and an USB memory stick, the program can be used, as required, directly or by installing a hard disk via a storage medium reader equipped in a computer system. Moreover, the program may be recorded in an external memory region (e.g. another computer) accessible from the computer system via an information and communication network, and the program may be used, as required, by directly from the external memory region or installing into a hard disk from the external memory region via the information and communication network.

(Computer-Readable Recording Medium)

The disclosed computer-readable recording medium includes the disclosed program stored thereon.

The computer-readable recording medium is not particularly limited and may be appropriately selected depending on the intended purpose. Examples of the computer-readable recording medium include integral hard disks, external hard disks, CD-ROMs, DVD-ROMs, MO disks, and USB memory sticks.

(Device for Calculating Binding Free Energy)

The disclosed device for calculating binding free energy is a device for calculating binding free energy between a binding calculation target molecule and a target molecule.

The device for calculating binding free energy includes at least an adding unit configured to perform a plurality of steps each including adding a distance restraint potential between the binding calculation target molecule and the target molecule. The device may further include other units, according to the necessity.

With the device for calculating binding free energy, anchor points in the binding calculation target molecules in the plurality of the steps are identical anchor points, and anchor points of the target molecules in the plurality of the steps are different anchor points.

The device for calculating binding free energy is configured to execute the method for calculating binding free energy.

Figure 9:
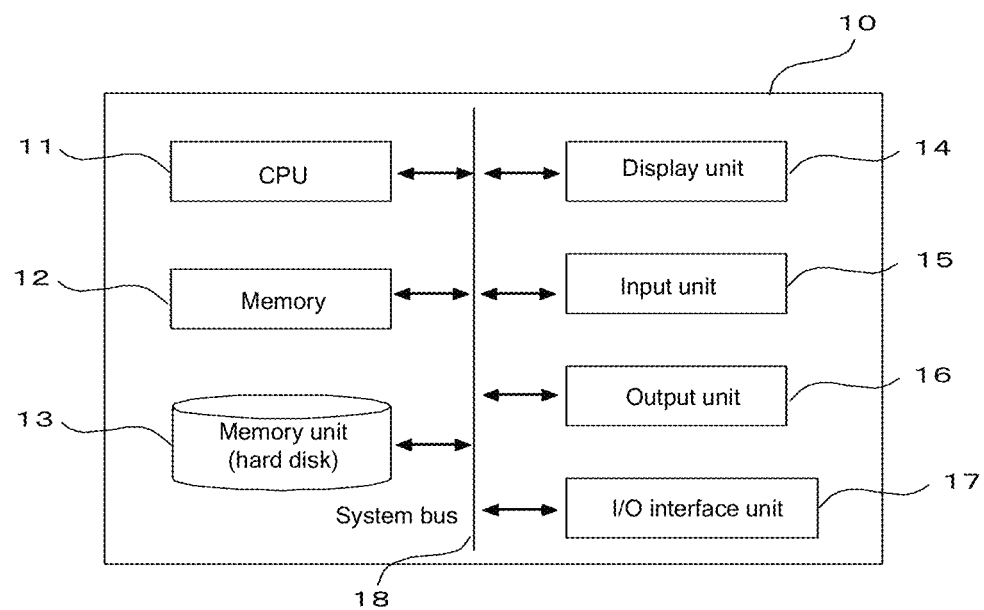
FIG. 9 illustrates a structural example of a hardware of the disclosed device for calculating binding free energy.

A structural example of a hardware of the disclosed device for calculating binding free energy is illustrated in FIG. 9.

For example, the device for calculating binding free energy 10 is composed by connecting CPU 11, a memory 12, a memory unit 13, a display unit 14, an input unit 15, an output unit 16, and an I/O interface unit 17 via a system bus 18.

The central processing unit (CPU) 11 is configured to perform calculation (e.g., four arithmetic operation, and relational operation), and control of operations of hardware and software.

The memory 12 is a memory, such as a random access memory (RAM), and a read only memory (ROM). The RAM is configured to store an operation system (OS) and application programs read from the ROM and the memory unit 13, and function as a main memory and work area of the CPU 11.

The memory unit 13 is a device for storing various programs and data. For example, the memory unit 13 is a hard disk. In the memory unit 13, programs to be executed by the CPU 11, data required for executing the programs, and an OS are stored.

The program is stored in the memory unit 13, loaded on the RAM (a main memory) of the memory 12, and executed by the CPU 11.

The display unit 14 is a display device. For example, the display unit is a display device, such as a CRT monitor, and a liquid crystal panel.

The input unit 15 is an input device for various types of data. Examples of the input unit include a key board, and a pointing device (e.g., a mouse).

The output unit 16 is an output device for various types of data. For example, the output unit is a printer.

The I/O interface unit 17 is an interface for connecting to various external devices. For example, the I/O interface unit enables input and output of data of CD-ROMs, DVD-ROMs, MO disks, and USB memory sticks.

The disclosed embodiments aim to solve the above-described various problems existing in the art, and to achieve the following object. Specifically, the present disclosure has an object to provide a method and device for calculating binding free energy where the method and device can improve calculation accuracy of binding free energy between a target molecule and a binding calculation target molecule, and a program for executing the method.

The disclosed method for calculating binding free energy can improve calculation accuracy of binding free energy between a binding calculation target molecule and a target molecule.

The disclosed device for calculating binding free energy can improve calculation accuracy of binding free energy between a binding calculation target molecule and a target molecule.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the sprit and scope of the invention.

What is claimed is:

1. A method of simulating over nano seconds of simulation time length by a simulation system to determine a drug candidate molecule, among a plurality of drug candidate molecules, by calculating a plurality of predicted binding free energy values between a target molecule and the plurality of drug candidate molecules, the method comprising:

by at least one processor of the simulation system,
a plurality of steps to predict the plurality of binding free energy values by calculating the plurality of predicted binding free energy values between the target molecule and the plurality of drug candidate molecules,
each predicted binding free energy value of the plurality of predicted binding free energy values calculated based on an alchemical route calculation method, when anchor points of the plurality of drug candidate molecules and anchor points of the target molecule are determined, the anchor points of the plurality of drug candidate molecules in the plurality of the steps being identical anchor points, the anchor points of the target molecule being different anchor points from each other, and each anchor point of the anchor points of the target molecule being determined using a plurality of atoms having small fluctuations in the target molecule, each step of the plurality of steps including, from among a plurality of values of distance restraint potential between the anchor points of the plurality of drug candidate molecules and the anchor points of the target molecule, adding a value of distance restraint potential between an anchor point of a drug candidate molecule among the plurality of drug candidate molecules and an anchor point of the target molecule among the anchor points of the target molecule, to calculating the a predicted binding free energy value between one of the plurality of drug candidate molecules and the target molecule;

an extracting step of extracting a smallest binding free energy value among of the plurality of predicted binding free energy values calculated in the plurality of steps, and a selecting step of selecting, from among the plurality of drug candidate molecules, a drug candidate molecule, based on the calculated plurality of predicted binding free energy values including the selected smallest binding free energy value, wherein in the plurality of the steps, the plurality of values of the distance restraint potential is added to the calculating of the plurality of predicted binding free energy values to cause excluding a metastable structure from at least one of sampling spaces so that the at least one of sampling spaces upon addition of the plurality of values of distance restraint potential includes a stable structure only and does not include the metastable structure as a binding structure between the target molecule and each of the plurality of drug candidate molecules, the excluding the metastable structure resulting in increasing simulation accuracy by the simulation system of the plurality of predicted binding free energy values over the nano seconds of simulation time length.

2. The method according to claim 1, wherein the anchor points of the drug candidate molecules are centers of gravity of the drug candidate molecules.

3. The method according to claim 1, wherein each of the anchor points of the target molecule is a center of gravity of a plurality of atoms having small fluctuations in the target molecule.

4. The method according to claim 1, wherein the alchemical route calculation method is based on an equation 1 below:

$$\Delta G_{bind}^{O} = -(\Delta G_{Solv}^{C} + \Delta G_{Solv}^{LJ} + \Delta G_{Sol}^{R} + \Delta G_{Cplx}^{R} + \Delta G_{Cplx}^{C} + \Delta G_{Cplx}^{LJ}) \quad \text{the equation 1}$$

where $\Delta G^{O}_{bind}$ indicates each respective predicted binding free energy value from the plurality of predicted binding free energy values, $\Delta G^{C}_{Solv}$ indicates predicted free energy of electrostatic interaction of a solvent, $\Delta G^{LJ}_{Solv}$ indicates predicted free energy of Van der Waals interaction of the solvent, $\Delta G^{R}_{Solv}$ indicates predicted free energy of a spring restraint potential of the solvent, $\Delta G^{C}_{Cplx}$ indicates predicted free energy of electrostatic interaction of a complex of the target molecule and each respective drug candidate molecule from the plurality of drug candidate molecules, $\Delta G^{LJ}_{Cplx}$ indicates predicted free energy of Van der Waals interaction of the complex, and $\Delta G^{R}_{Cplx}$ indicates predicted free energy of a spring restraint potential of the complex.

5. The method according to claim 1,
wherein one calculation of a predicted binding free energy value among the plurality of predicted binding free energy values is performed using a value of distance restraint potential added between an anchor point of a drug candidate molecule among the plurality of drug candidate molecules and one anchor point among the anchor points of the target molecule, and wherein another calculation of binding free energy is performed using a distance restraint potential added between the anchor point of the drug candidate molecule among the plurality of drug candidate molecules and another anchor point among the anchor points of the target molecule that is different from the one anchor point of the target molecule.

6. The method according to claim 5,
wherein the one calculation of a predicted binding free energy value among the plurality of predicted binding free energy values is calculation of a first predicted binding free energy value, and wherein the other calculation of binding free energy is calculation of a second binding free energy value.

7. A simulation device to determine a drug candidate molecule, the device comprising:

a central processing unit to simulate over nano seconds of simulation time length to determine a drug candidate molecule, among a plurality of drug candidate molecules, by calculating a plurality of predicted binding free energy values between a target molecule and the plurality of drug candidate molecules, the central processing unit configured to perform a plurality of steps to predict the plurality of predicted binding free energy values by calculating the plurality of predicted binding free energy values between the plurality of drug candidate molecules and the target molecule, each predicted binding free energy value of the plurality of predicted binding free energy values calculated based on an alchemical route calculation method, when anchor points of the plurality of drug candidate molecules and anchor points of the target molecule are determined, the anchor points of the plurality of drug candidate molecules in the plurality of the steps being identical anchor points, the anchor points of the target molecule being different anchor points from each other, and each anchor point of the anchor points of the target molecule being determined using a plurality of atoms having small fluctuations in the target molecule, each step of the plurality of steps including, from among a plurality of values of distance restraint potential between the anchor points of the plurality of drug candidate molecules and the anchor points of the plurality of drug candidate molecules, adding a value of distance restraint potential between an anchor point of a drug candidate molecule among the plurality of drug candidate molecules and an anchor point of the target molecule among the anchor points of the target molecule, to calculating a predicted binding free energy value between one of the plurality of drug candidate molecules and the target molecule, extract a smallest binding free energy value among the plurality of predicted binding free energy values calculated in the plurality of steps, and select, from among the plurality of drug candidate molecules, a drug candidate molecule, based on the calculated plurality of predicted binding free energy values including the smallest binding free energy predicted value, wherein in the plurality of the steps, the plurality of values of the distance restraint potential is added to the calculating of the plurality of predicted binding free energy values to cause excluding a metastable structure from at least one of sampling spaces so that the at least one of sampling spaces upon addition of the distance restraint potential includes a stable structure only and does not include the metastable structure as a binding structure between the target molecule and each of the plurality of drug candidate molecules, the excluding the metastable structure resulting in increasing simulation accuracy by the simulation device of the plurality of predicted binding free energy values over the nano seconds of simulation time length.

8. The device according to claim 7, wherein the anchor points of the drug candidate molecules are centers of gravity of the drug candidate molecules.

9. The device according to claim 7, wherein each of the anchor points of the target molecule is determined using a plurality of atoms having small fluctuations in the target molecule.

10. The device according to claim 7, wherein the alchemical route calculation method is based on an equation 1 below:

$$\Delta G_{bind}^{O} = -(\Delta G_{Solv}^{C} + \Delta G_{Solv}^{LJ} + \Delta G_{Sol}^{R} + \Delta G_{Cplx}^{R} + \Delta G_{Cplx}^{C} + \Delta G_{Cplx}^{LJ}) \quad \text{the equation 1}$$

where $\Delta G^{O}_{bind}$ indicates each respective predicted binding free energy value from the plurality of predicted binding free energy values, $\Delta G^{C}_{Solv}$ indicates predicted free energy of electrostatic interaction of a solvent, $\Delta G^{LJ}_{Solv}$ indicates predicted free energy of Van der Waals interaction of the solvent, $\Delta G^{R}_{Solv}$ indicates predicted free energy of a spring restraint potential of the solvent, $\Delta G^{C}_{Cplx}$ indicates predicted free energy of electrostatic interaction of a complex of the target molecule and each respective drug candidate molecule from the plurality of drug candidate molecules, $\Delta G^{LJ}_{Cplx}$ indicates predicted free energy of Van der Waals interaction of the complex, and $\Delta G^{R}_{Cplx}$ indicates predicted free energy of a spring restraint potential of the complex.

11. The device according to claim 7, wherein one calculation of a predicted binding free energy value among the plurality of predicted binding free energy values is performed using a value of distance restraint potential added between an anchor point of a drug candidate molecule among the plurality of drug candidate molecules and one anchor point among the anchor points of the target molecule, and wherein another calculation of binding free energy is performed using a distance restraint potential added between the anchor point of the drug candidate molecule among the plurality of drug candidate molecules and another anchor point among the anchor points of the target molecule that is different from the one anchor point of the target molecule.

12. The device according to claim 11, wherein the one calculation of the predicted binding free energy value is calculation of first predicted binding free energy value, and wherein the other calculation of binding free energy is calculation of a second predicted binding free energy value.

13. A non-transitory computer-readable storage medium storing a program that causes an information processing apparatus to execute a process of simulating over nano seconds of simulation time length by a simulation information processing apparatus to determine a drug candidate molecule, among a plurality of drug candidate molecules, by calculating a plurality of predicted binding free energy values between a target molecule and the plurality of drug candidate molecules, the process comprising:

By at least one processor of the simulation information processing apparatus, identifying first anchor points respectively of the plurality of drug candidate molecules;

identifying, among a plurality of anchor points of the target molecule, a second anchor point of the target molecule and a third anchor point of the target molecule different from the second anchor point;

adding first distance restraint potential values between the first anchor points respectively of the plurality of drug candidate molecules and the second anchor point of the target molecule to calculating, among the plurality of binding free energy values, first predicted binding free energy values between the plurality of drug candidate molecules and the target molecule using, respectively, the first distance restraint potential values, and calculating the first predicted binding free energy values;

adding second distance restraint potential values between the first anchor points respectively of the plurality of drug candidate molecules and the third anchor point of the target molecule to calculating, among the plurality of binding free energy values, second predicted binding free energy values between the plurality of drug candidate molecules and the target molecule using, respectively, the second distance restraint potential values, and calculating the second predicted binding free energy values;

determining smallest values, respectively for the plurality of drug candidate molecules, between the first predicted binding free energy values and the second predicted binding free energy values, to increase calculation accuracy of the plurality of predicted binding free energy values between the plurality of drug candidate molecules and the target molecule based on an alchemical route calculation method, wherein each of the anchor points of the target molecule is determined using atoms having small fluctuations in the target molecule, and wherein the first distance restraint potential values and the second distance potential values are added to, respectively, to calculating the first predicted binding free energy values and calculating the second predicted binding free energy values to cause excluding a metastable structure from at least one of sampling spaces so that the at least one of sampling spaces upon addition of the first distance restraint potential values and the second distance restraint potential values includes a stable structure only and does not include a metastable structure as a binding structure between the target molecule and each of the plurality of drug candidate molecules, the excluding the metastable structure resulting in increasing simulation accuracy by the information processing apparatus of the plurality of predicted binding free energy values over the nano seconds of simulation time length.

* * * * *